US008747735B2

(12) United States Patent
Homer

(10) Patent No.: US 8,747,735 B2
(45) Date of Patent: Jun. 10, 2014

(54) ELECTRONIC SCENT GENERATOR

(76) Inventor: Gregg S. Homer, Laguna Beach, CA (US)

( * ) Notice: Subject to any disclaimer, the term of this patent is extended or adjusted under 35 U.S.C. 154(b) by 49 days.

(21) Appl. No.: 13/458,081

(22) Filed: Apr. 27, 2012

(65) Prior Publication Data
US 2013/0284821 A1 Oct. 31, 2013

(51) Int. Cl.
A61L 9/00 (2006.01)
A61L 2/00 (2006.01)
A62B 7/08 (2006.01)
B06B 1/00 (2006.01)
A61L 2/22 (2006.01)
A61L 9/04 (2006.01)
A61L 9/14 (2006.01)
A61L 9/18 (2006.01)

(52) U.S. Cl.
CPC .... A61L 2/22 (2013.01); *A61L 9/00* (2013.01); *A61L 9/04* (2013.01); *A61L 9/14* (2013.01); *A61L 9/18* (2013.01)
USPC ...... 422/22; 422/5; 422/21; 422/24; 422/123; 422/124; 422/125; 422/127; 422/128

(58) Field of Classification Search
CPC .............. A61L 2/22; A61L 9/00; A61L 9/04; A61L 9/14; A61L 6/18
USPC ........... 422/5, 20–22, 24, 123–125, 127–128, 422/306; 261/26, 100
See application file for complete search history.

(56) References Cited

U.S. PATENT DOCUMENTS

| | | | |
|---|---|---|---|
| 6,390,453 B1 * | 5/2002 | Frederickson et al. | ......... 261/26 |
| 2002/0114744 A1 | 8/2002 | Chiao et al. | |
| 2002/0146361 A1 | 10/2002 | Gardner et al. | |
| 2003/0109048 A1 | 6/2003 | Young et al. | |
| 2004/0003812 A1 | 1/2004 | Manne | |
| 2004/0024496 A1 | 2/2004 | Young et al. | |
| 2007/0058144 A1 | 3/2007 | Olsen et al. | |
| 2007/0090550 A1 | 4/2007 | Manne | |
| 2007/0138326 A1 | 6/2007 | Hu | |
| 2007/0258849 A1 * | 11/2007 | Kent | ................. 422/5 |
| 2008/0043204 A1 | 2/2008 | Guo | |
| 2008/0110343 A1 | 5/2008 | Cheng | |
| 2008/0313789 A1 | 12/2008 | Manne | |
| 2009/0054116 A1 | 2/2009 | Hakunti et al. | |
| 2009/0147104 A1 | 6/2009 | Wang | |
| 2009/0196587 A1 | 8/2009 | Cheung | |
| 2010/0096376 A1 | 4/2010 | Hsiao | |
| 2010/0155414 A1 | 6/2010 | Hu | |
| 2010/0270388 A1 | 10/2010 | Liu | |
| 2011/0253800 A1 | 10/2011 | Doty | |

* cited by examiner

*Primary Examiner* — Monzer R Chorbaji
(74) *Attorney, Agent, or Firm* — Aka Chan LLP

(57) ABSTRACT

The invention is directed to the application of EMR to one or more elements for the purpose of generating a scent response in humans. Electronic scents may be transmitted on a standalone basis, unaccompanied by other sensory stimulus, or as part of a multisensory experience. Examples of multisensory experiences include theatrical motion pictures, television programming, sound recordings, or e-books accompanied by one or more scents. These scents may be coordinated with content elements, such as the scent of horses accompanying the motion picture "High Noon," the scents of beer and leather accompanying a sound recording of "When You're a Jet" from "West Side Story," or the musty scent of a cellar in an e-book version of Poe's "The Cask of Amontillado."

18 Claims, 4 Drawing Sheets

Electronic Scent Generator v.1

Electronic Scent Generator v.3

ELECTRONIC SCENT GENERATOR

BACKGROUND OF THE INVENTION

Scent plays an important role in human behavior. Scents can evoke powerful emotions. One need only recall the flood of emotions reported by Marcel Proust in "Remembrance of Things Past" when he dipped his madeleine into his tea and their unique blend of odors were released. This may be due to the close anatomical ties between the olfactory system and the limbic system and hippocampus, areas of the brain that have long been known to be involved in emotion and place memory, respectively. See Nieuwenhuys, The Greater Limbic System, the Emotional Motor System, and the Brain, 107 Prog. Brain Res. 551 (1996). Some commentators have suggested that 75% of emotions are generated by smell. See, e.g., Bell & Bell, Future Sense: Defining Brands Through Scent, 38 J. Market. Soc. 38 (2007).

By virtue of its effect on emotions, scent can play a role in a variety of common behaviors. By way of example, scent is implicated in mate selection. Men exposed to the scent of an ovulating woman subsequently displayed higher levels of testosterone than did men exposed to the scent of a non-ovulating woman or a control scent, suggesting that olfactory cues signaling women's levels of reproductive fertility are associated with specific endocrinological responses in men that are linked to the initiation of romantic courtship. See Miller, Scent of a Woman: Men's Testosterone Responses to Olfactory Ovulation Cues, 21 Psychological Science 276-83 (2010). Scent may also play a role in therapeutic medical treatment. In women, the sense of olfaction is strongest around the time of ovulation, significantly stronger than during other phases of the menstrual cycle and also stronger than the sense in males. See Navarrete-Palacios, et al., Lower Olfactory Threshold During the Ovulatory Phase of the Menstrual Cycle, 63 Biolog. Psychol. 269-79 (2003).

The field of aromatherapy posits that essential oils and other aromatic compounds may alter a person's mind, mood, cognitive function, and health. See Edris, Pharmaceutical and Therapeutic Potentials of Essential Oils and Their Individual Volatile Constituents: A Review, 21 Phytotherapy Res. 308-23 (2007).

Scents can also influence consumer shopping habits. In 2006, scent marketing was touted as one of the top ten trends to watch. See Thomaselli, Trends to Watch in 2007, 77 Advertising Age 10 (2006). Many retailers, hotels, and restaurants investing in scent marketing with the belief that carefully selected scents will influence consumer spending, attract customers, and create memorable brands. See Dowdey, Does what you smell determine what you buy?, in How Stuff Works (Dec. 27, 2007), available on Mar. 17, 20012, at <http://money.howstuffworks.com/scent-marketing.htm>. As a result, the scent marketing industry is a $100 million business and is predicted to reach up to $1 billion within the next few years. See Ravn, Smells Like Sales, L.A. Times F-1 (Aug. 20, 2007).

The importance of scent to humans is reflected in the size of the international perfume industry. Current retail sales are between $25 billion and $30 billion worldwide. Burr, Perfumers Breathe in Sales Data, and Strategize, N.Y. Times, Bus. Sec. (Jun. 19, 2009). Sales are expected to exceed $33 billion by 2015. Global Industry Analysts, Inc., Fragrances and Perfumes—A Global Strategic Business Report (2011).

Most scents are derived from organic materials—plants, animals, and other natural sources. Most scents are derived from plants, including plant barks (such as cinnamon, cascarilla, and sassafras), flowers and blossoms (such as rose, jasmine, tuberose, and narcissus), fruits (such as orange, lemon, and lime), leaves and twigs (such as lavender, patchouli, and sage), resins (such as frankincense, myrrh, and pine), roots, rhizomes and bulbs (such as iris, vetiver, and ginger), seeds (such as coriander, cardamom, and anise), and woods (such as sandalwood, cedar, and juniper). Animal scent sources include ambergris (from the sperm whale), castoreum (form the North American beaver), musk (from the civet—a relative of the mongoose—or the Asian musk deer), hyraceum (the petrified excrement of the Rock Hyrax), and honeycomb (from the honeycomb of the honeybee). Other natural sources include lichens (such as oakmoss and treemoss thalli) and seaweed (such as *Fucus vesiculosus*). Other scents comprise synthesized scents. Synthetics can provide scents not found in nature (such as Calone), as well as scents too expensive to harvest from natural sources (such as linalool, orchid scents, and white musk) and fragrances that, in their natural form, are toxic to humans (such as coumarin, which is a carcinogen).

Various electronic devices have been proposed for the generation of scents. Examples of commercially available devices include the Scent Generator Classic (Biophysical Human Research Institute, Ljubljana, Slovenia), Fragrance Communication (NTT Communications Corporation, Tokyo, Japan), Odoravision (OlfAction, Paris, France), Scent-Dome (TriSenx, Inc., Savannah, Ga., USA), Kaori Web (K-Opticom Corporation, Tokyo, Japan), and the ScentScape Programmable Aroma Generator (Scent Sciences Corporation, San Jose, Calif., USA). Each of these devices store one or more scented substances (which may be organic or synthetic), the innate scents of which are activated with heat. In some cases, two or more substances are activated, and the activated scents combine to form a different scent.

The devices of the prior art are subject to several limitations. One such limitation is that the number of scents a device can generate is limited by the number of scented substances stored in the device. Even taking combinatorial scents into account, the capacity of the device to generate a vast number of scents requires storage of a vast number of substances, which, albeit possible, impedes the potential for broad distribution to consumers.

Another limitations of the prior art is that none of these devices includes a mechanism for suppressing or extinguishing a scent once generated. Instead, the scent continues to be activated until the activating stimulus dissipates. By analogy to musical notes, this limitation is akin to a piano with no damper, wherein each note played would continue to be heard until the vibration of the string ceases. This limitation could be partially overcome by subjecting the scent substances to a stimulus antipodal to the activating mechanism. By way of example, if heat is used to activate a given substance, the scent could be suppressed or "damped" by cooling the substance with a cryogen liquid or gas (such as argon, carbon dioxide, chlorodifluoromethane, chloropentafluoroethane, chlorotrifluoromethane, clean dry air, compressed air, dichlorofluoromethane, dichlorofluoromethane, floroform, helium, hexafluoroethane, krypton, neon, nitrogen, perfluoropentane, sulfur hexafluoride, tetrafluoromethane, trichlorofluoromethane, trichlorofluoromethane, or xenon). This would require, however, that the device include both the material and application mechanism of the antipodal stimulus, thereby adding more size, weight, and complexity to the device. Moreover, these antipodal materials can be harmful to the environment, the health and safety of the user, or both. The health and safety risks of cryogens, for example, include contact burns, frostbite, asphyxiation, toxicity, and hypothermia. In addition, even if the scent activation is suppressed, those scent molecules already released into the atmosphere would continue to linger until they dissipate in due course. The value of electronic scent generation is control over the scents produced. The inability to suppress or extinguish a scent fully at will is a limitation that undermines the benefits of the device.

A third limitations of the prior art is size and weight. In order to store a critical mass of scent substances and the mechanism required to activate the same, these scent generating devices are necessarily large. In addition, their portability is limited by the risks associated with leakage of scent substances and activation stimuli (such as heat).

There is a need for an electronic scent generator that is able to produce a vast array of scents without having to store a large number of scent substances and is further able to extinguish those scents as and when desired. Ideally, the device would be sufficiently compact to occupy desktops and living rooms and would be susceptible to production in both portable and wearable versions.

BRIEF SUMMARY OF THE INVENTION

The invention is directed to the application of EMR to one or more elements for the purpose of generating a scent response in humans. The invention may include its own computer system or it may be connected to a separate computer system. If the separate computer is local, the device may be connected to the computer wirelessly or via a USB cable or other data transmission medium. If the separate computer is remote (such as a remote or network server), the device may be connected to the computer via any communications network, including, without limitation, internet, pier-to-pier, LAN, WAN, cable, satellite, telephone lines, cellular, microwave, radio, light, and laser.

Electronic scents may be transmitted on a stand-alone basis, unaccompanied by other sensory stimulus, or as part of a multisensory experience. Examples of multisensory experiences include theatrical motion pictures, television programming, sound recordings, or e-books accompanied by one or more scents. These scents may be coordinated with content elements, such as the scent of horses accompanying the motion picture "High Noon," the scents of beer and leather accompanying a sound recording of "When You're a Jet" from "West Side Story," or the musty scent of a cellar in an e-book version of Poe's "The Cask of Amontillado."

Electronic scent generation could also be (a) used as deodorizers, air fresheners, or ambient fragrance generators for any location (including, without limitation, homes, offices, classrooms, theaters, conference halls, boats, airplanes, trains, automobiles, stores, malls, casinos, and hospitals), which scents could change based on the time of day, amount of motion, amount of light, sound level, sound pitch, temperature, or other environmental factors, (b) worn on the body, such as scent-generating pendants, pins, wrist bands, buttons, rings, and earrings, (c) used to receive scented e-mails containing scent frequencies and amplitudes, (d) used to deliver scented on-line advertising materials, such as those for perfumes, shampoos, and body lotions, (e) used for scent-generating, in-store, point-of-purchase displays, (f) used to provide web sites with clickable scents for sampling of product fragrances or for pure entertainment value, (g) used to provide websites with programmed scents based on the visitor IP address or cookie-reflected browsing habits (which scents may represent product scents or may serve as an ambient element to influence visitor consumption). Electronic scent generators also offer the possibility of artistic concatenations of scents, wherein scents are combined harmonically, melodically, or both to create scent symphonies.

By adding an electronic scent detector to the scent generator, the scent generator could be used for "scent cancelation" by transmitting scent waves with the same amplitudes but inverted phases (also known as antiphases) as the ambient scent waves. The inverted and ambient scent waves would then combine to form a new wave (let us call this "scent interference"), and these weaves would effectively cancel each other out (let us call this "scent phase cancellation").

Electronically generated scents could also be used to supplement or cancel tastes. The sense of taste is anatomically related to the sense of smell, and scent can greatly affect taste. Sweet scents could be transmitted to children while eating their vegetables or taking medicines to make them more palatable. Similarly, unhealthful dietary cravings could be satisfied by transmitting scents to dieters while they are eating healthy foods.

The invention could also be used for educational purposes—whether on-line or in the classroom. Botany students could, for example, learn the scents of various plants and flowers, and oenology students could learn to differentiate wines based on distinctive bouquets.

Electronic scents could also serve as signals. Putrid scents, for example, might signal hazardous conditions. This could be particularly helpful for those with limited auditory or visual acuity, particularly since the sense of olfaction tends to become sharper as other senses decline. Scent signals could also be used to signal interest to or attract a potential mating partner. Even on-line dating sites might have scent sharing capabilities as an additional means of identifying common ground with potential mates.

The invention could be used to influence animal behavior. A cat-urine scent generator in the basement or attic, for example, would keep rats away, and a vinegar-sent generator might discourage the pet dog from urinating indoors. Because animal olfaction tends to be far more sensitive than human olfaction, scents may be capable of influencing animal behavior without detection by humans.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
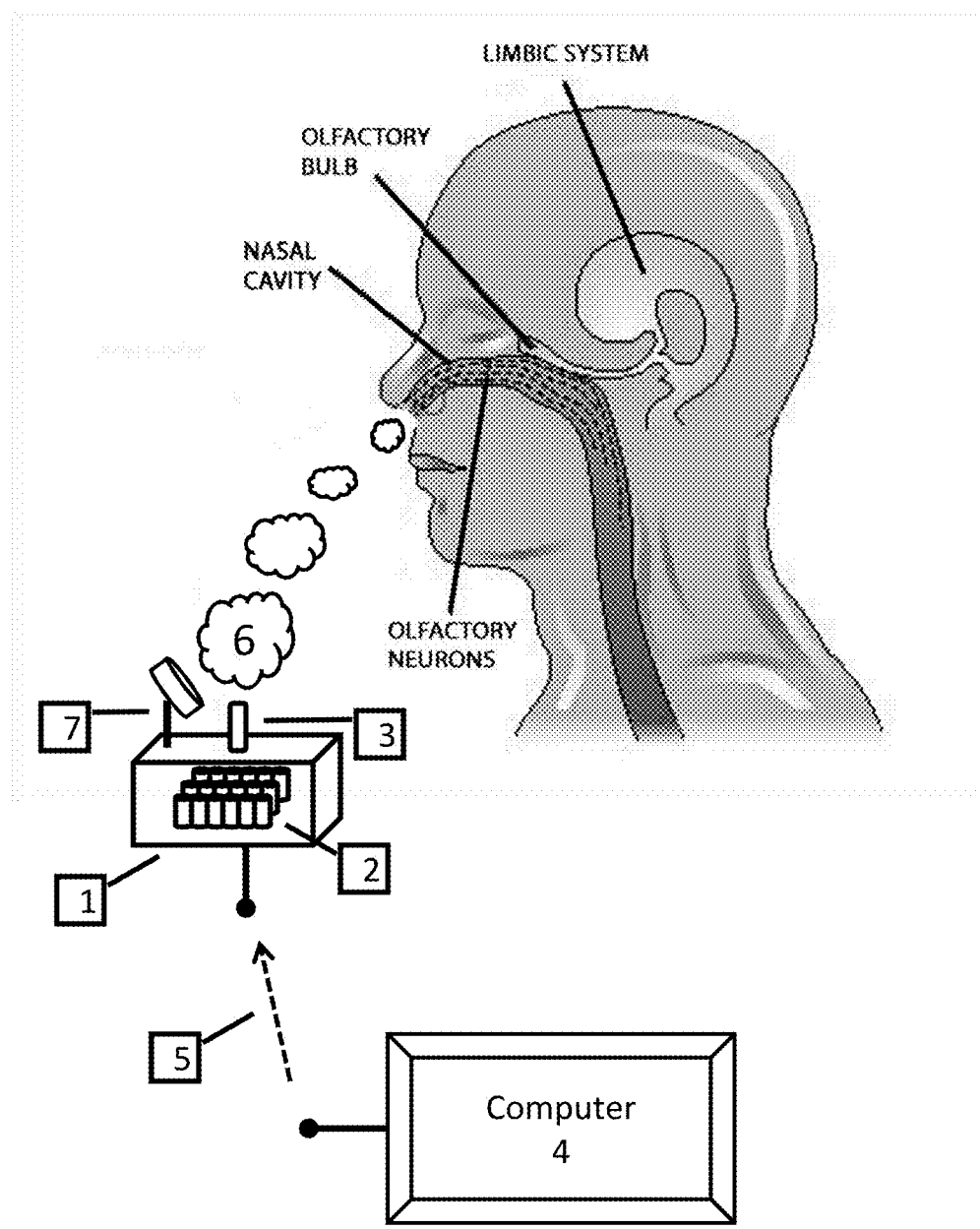
FIG. 1 shows aspects of a particular embodiment of the invention, as more particularly described in the specification.

There are currently two predominant theories of human olfaction: the steric theory (also known as the shape or lock-and-key theory) and the vibrational theory. The steric theory posits that every odor molecule that enters our nose has a specific shape that fits a specific receptor, like a key fits a lock. When a molecule of lemon, for example, fits into an olfactory receptor for lemon, we perceive a lemon smell. See Amoore, Molecular Basis of Odor (1970); Moncrieff, What is Odor—A New Theory, 54 Am. Perfumer 453 (1949). There are, however, several challenges to the steric theory. First, similarly shaped molecules with different molecular vibrations have different smells, and, conversely, differently shaped molecules with similar molecular vibrations have similar smells. Second, smaller molecules of similar shape—which should be confused more often than larger molecules—have extremely distinctive odors. And third, scent descriptions in the olfaction literature correlate more strongly with their vibrational frequencies than with their molecular shape.

The vibrational theory maintains that the smell of a molecule is determined by intramolecular vibrations (frequency and amplitude), rather than by the shape of the molecule. See Wright, The Sense of Smell (1982); Dyson, The Scientific Basis of Odour, 57 Chem. Ind. 647-51 (1938). A more recent version of the theory is based on "inelastic electron tunneling," which argues that that when the olfactory receptor binding site is empty, electrons are unable to tunnel across the binding site because no empty levels are available at the appropriate energy. When an odorant occupies the binding site, electrons can lose energy during tunneling by exciting its vibrational mode. This happens only if the energy of the vibrational mode equals the energy gap between the filled and empty levels. Turin, A Spectroscopic Mechanism for Primary Olfactory Reception, 21 Chem. Senses 773-91 (1996). Turin proposes that the vibrational range for odorants is typically from 50 cm^-1 to 3400 cm^-1 (in wavenumbers), which falls roughly in the mid- and far-infrared ranges ("IR") of the electromagnetic ("EMR") spectrum. Turin, A Method for the Calculation of Odor Character from Molecular Structure, 216 J. Theor. Biol. 367, 368 (2002).

The invention is directed to the application of EMR to one or more elements for the purpose of generating a scent response in humans. As used in this disclosure, "EMR" includes any form of electromagnetic radiation, whether now known or hereafter discovered, whether in the form of sound, heat, light, or otherwise, and whether consisting of radio frequency, ultrasound, microwave, IR, visible light, ultraviolet, x-ray, t-ray, gamma ray, or otherwise. The term "EMR" is not intended to restrict the form of radiation in terms of monochromaticity (i.e., composed of one or more than one different wavelength), directionality (i.e., produce a single non-divergent spot or radiate in several different directions), or coherence (i.e., the waves produced consist of a single phase relation or of multiple phase relations). Moreover, the frequency of the EMR can be any frequency within the EMR spectrum, including, without limitation, extremely low frequency sound radiation (with a frequency of 3 Hz) to gamma radiation (with a frequency of 300 EHz). The EMR can be delivered in a continuous wave or in pulses, and the pulse width may be any time interval, including microseconds, nanoseconds, picoseconds, femtoseconds, or attoseconds. If pulsed, any repetition rate may be used, including, without limitation, repetition rates from 1 Hz to 100 THz. In addition, any energy output may be used, and any energy density may be created at the target treatment side, including, without limitation, energy outputs from 1 W to 5000 W. In addition, any gain medium may be used, including, without limitation, glass, solid, liquid, gas, crystal, or semiconductor.

EMR sources include, without limitation, lasers (such as the Tunable Quantum Cascade IR Diode Lasers from Alpes Lasers SA, Neuchâtel, Switzerland), filaments (such as the tungsten NiCr, and Kanthal filaments from HelioWorks, Inc., Santa Rosa, Calif.), silicon nitride emitters (such as the IR-18 from HawkEye Technologies, LLC, Milford, Conn.), carbon emitters (such as the IR-50 series from HawkEye Technologies, LLC, Milford, Conn.), light-emitting diodes (LEDs), such as the mid-IR LEDs from Ioffe LED, Ltd., Saint Petersburg, Russia), and resistors (such as the IR-12 Series Miniature 8 to 11 Watt Infrared Emitter from HawkEye Technologies, LLC, Milford, Conn.).

The term "scents," as used herein, includes scents, fragrances, odors, odorants, smells, pheromones, and other vomeronasal and olfactory (main and accessory) stimulants. The term includes stimulants that are pleasant and unpleasant, organic and synthetic, and nature and unnatural.

"Elements," as used in this disclosure, includes all chemical elements, isotopes, molecules, compounds, and mixtures, whether gases, liquids, or solids, whether primordial, transient, or synthetic, and whether now known or hereafter discovered.

The invention may include its own computer system or it may be connected to a separate computer system. An exemplary computer system can include software, monitor, cabinet, keyboard, and mouse. The cabinet can house familiar computer components, such as a processor, memory, mass storage devices, and the like. Mass storage devices may include mass disk drives, floppy disks, Iomega ZIP™ disks, magnetic disks, fixed disks, hard disks, CD-ROMs, recordable CDs, DVDs, DVD-R, DVD-RW, flash and other non-volatile solid-state storage, tape storage, reader, and other similar media, and combinations of these. A binary, machine-executable version of the software of the present invention may be stored or reside on mass storage devices. Furthermore, the source code of the software of the invention may also be stored or reside on mass storage devices (e.g., magnetic disk, tape, or CD-ROM). A computer system may also include subsystems such as central processor, system memory, input/output (I/O) controller, display adapter, serial or universal serial bus (USB) port, network interface, and speaker. The invention may be used with computer systems with additional or fewer subsystems. For example, a computer system could include more than one processor (i.e., a multiprocessor system), or a system may include a cache memory. If the separate computer is local, the device may be connected to the computer wirelessly or via a USB cable or other data transmission medium. If the separate computer is remote (such as a remote or network server), the device may be connected to the computer via any communications network, including, without limitation, internet, pier-to-pier, LAN, WAN, cable, satellite, telephone lines, cellular, microwave, radio, light, and laser.

Electronic scents may be transmitted on a stand-alone basis, unaccompanied by other sensory stimulus, or as part of a multisensory experience. Examples of multisensory experiences include theatrical motion pictures, television programming, sound recordings, or e-books accompanied by one or more scents. These scents may be coordinated with content elements, such as the scent of horses accompanying the motion picture "High Noon," the scents of beer and leather accompanying a sound recording of "When You're a Jet" from "West Side Story," or the musty scent of a cellar in an e-book version of Poe's "The Cask of Amontillado."

Electronic scent generation could also be (a) used as deodorizers, air fresheners, or ambient fragrance generators for any location (including, without limitation, homes, offices, classrooms, theaters, conference halls, boats, airplanes, trains, automobiles, stores, malls, casinos, and hospitals), which scents could change based on the time of day, amount of motion, amount of light, sound level, sound pitch, temperature, or other environmental factors, (b) worn on the body, such as scent-generating pendants, pins, wrist bands, buttons, rings, and earrings, (c) used to receive scented e-mails containing scent frequencies and amplitudes, (d) used to deliver scented on-line advertising materials, such as those for perfumes, shampoos, and body lotions, (e) used for scent-generating, in-store, point-of-purchase displays, (f) used to provide web sites with clickable scents for sampling of product fragrances or for pure entertainment value, (g) used to provide websites with programmed scents based on the visitor IP address or cookie-reflected browsing habits (which scents may represent product scents or may serve as an ambient element to influence visitor consumption). Electronic scent generators also offer the possibility of artistic concatenations of scents, wherein scents are combined harmonically, melodically, or both to create scent symphonies.

By adding an electronic scent detector to the scent generator, the scent generator could be used for "scent cancelation" by transmitting scent waves with the same amplitudes but inverted phases (also known as antiphases) as the ambient scent waves. The inverted and ambient scent waves would then combine to form a new wave (let us call this "scent interference"), and these weaves would effectively cancel each other out (let us call this "scent phase cancellation"). Electronic scent detectors are well-known in the art. See Haddad, et al., Predicting Odor Pleasantness with an Electronic Nose, 6 PLoS Comput. Biol. 1 (2010); Persaud & Dodd, Analysis of Discrimination Mechanisms in the Mammalian Olfactory System Using a Model Nose, 299 Nature 352-55 (1982). Some models are now commercially available. See, e.g., the E-Nose (E-Nose Pty Ltd, Eveleigh, NSW).

Electronically generated scents could also be used to supplement or cancel tastes. The sense of taste is anatomically related to the sense of smell, and scent can greatly affect taste. Sweet scents could be transmitted to children while eating their vegetables or taking medicines to make them more palatable. Similarly, unhealthful dietary cravings could be satisfied by transmitting scents to dieters while they are eating healthy foods.

The invention could also be used for educational purposes—whether on-line or in the classroom. Botany students could, for example, learn the scents of various plants and flowers, and oenology students could learn to differentiate wines based on distinctive bouquets.

Electronic scents could also serve as signals. Putrid scents, for example, might signal hazardous conditions. This could be particularly helpful for those with limited auditory or visual acuity, particularly since the sense of olfaction tends to become sharper as other senses decline. Scent signals could also be used to signal interest to or attract a potential mating partner. Even on-line dating sites might have scent sharing capabilities as an additional means of identifying common ground with potential mates.

The invention could be used to influence animal behavior. A cat-urine scent generator in the basement or attic, for example, would keep rats away, and a vinegar-sent generator might discourage the pet dog from urinating indoors. Because animal olfaction tends to be far more sensitive than human olfaction, scents may be capable of influencing animal behavior without detection by humans.

The scent-generating device may be any size or shape, may be powered by any source (including alternating current, batteries, solar panels, or hand crank), and may be portable (such as handheld devices) or non-portable. These devices may also be installed permanently or fully removable.

Scent frequencies and amplitudes may be stored locally or remotely in volatile or nonvolatile memory. Non-volatile storage includes, without limitation, hard disks and drives, ROM, F-RAM, flash memory and drives, CD-ROMs, memory cards, digital tape cassettes, smart cards, floppy disks and diskettes, microchips, magnetic tape, optical discs, paper tape, and punched cards. Volatile storage includes, without limitation, RAM (including DRAM and SRAM), delay line memory, and Williams tube.

Figure 2:
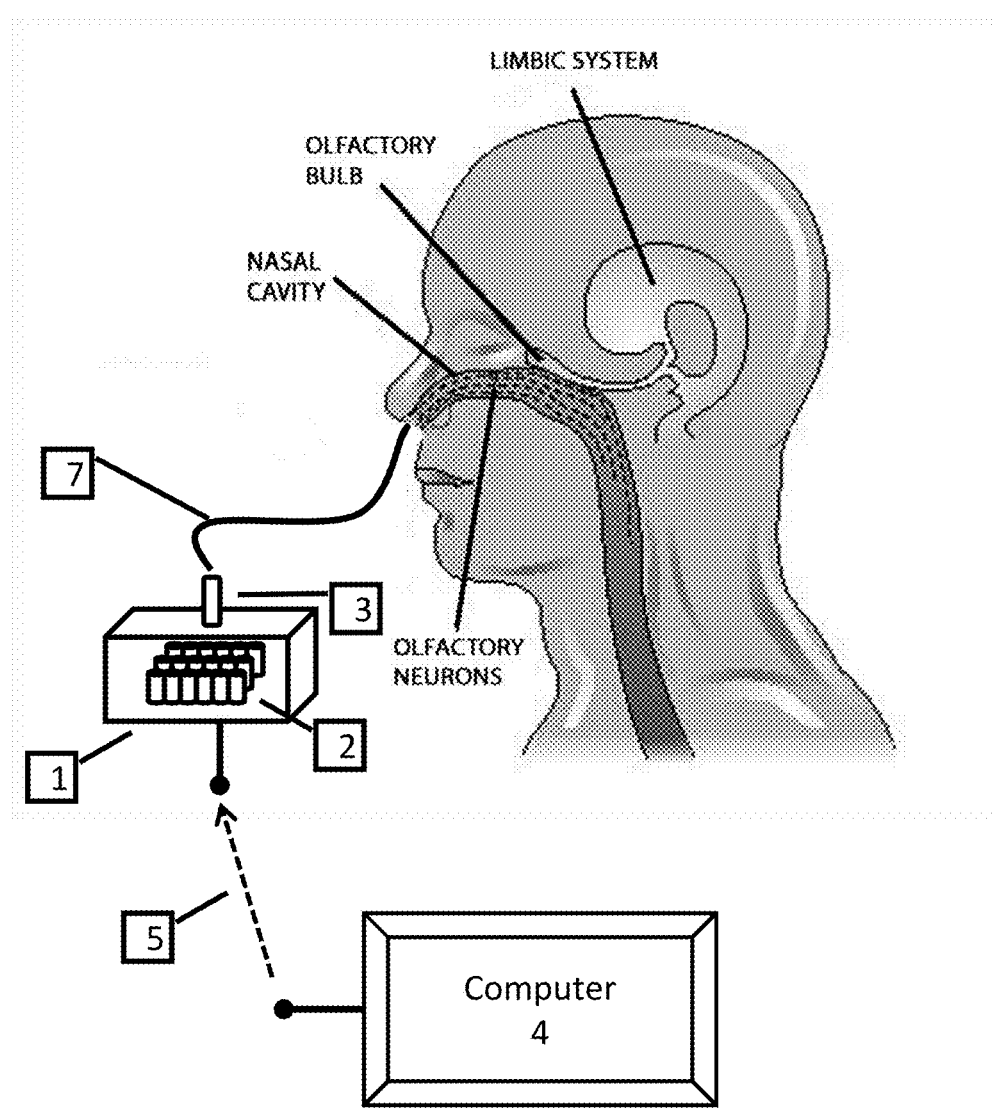
FIG. 2 shows aspects of a particular embodiment of the invention, as more particularly described in the specification.

In one embodiment of the invention (see FIG. 1), a scent generator comprises an electronic device (1) powered by direct current. The device includes multiple sets of light-emitting diodes or LEDs (2). Each set of LEDs is separately tunable (i.e., frequency variability) within the mid- and far-IR ranges. The LED output is directed to a sapphire vial (3) containing a mixture of molecules of various shapes and sizes based on the shapes and sizes of a variety of olfactory receptors. Ideally, this mixture has little or no odor prior to its activation by the LED output. The frequencies of the LED output are tuned based on signals received from a computer (4) on which a proprietary olfaction software program has been installed. The scent generating device is connected to the computer wirelessly. An e-mail is received on the computer. The email contains a scent code for musk. The scent code is received by the software program, which transmits (5) to the scent generating device the specific frequencies for musk. According to Turin, the musk scent has three prominent bands around 700, 1500, and 2200 $cm^{-1}$, and a weak band around 1000 $cm^{-1}$, between the first and the second bands (measured in wavenumbers). See Turin, A Method for the Calculation of Odor Character from Molecular Structure, supra at 374. The molecular mixture is activated by the frequencies of the LED output, producing the scent of musk (6). A small fan may be installed adjacent the opening of the sapphire vial (7). The fan would drive the scent of the molecular mixture towards the user's nose. The user perceives the scent of musk until the LED output is terminated and the molecules and/or frequencies dissipate. In one version of this embodiment, the fan drives the molecules into the atmosphere in the vicinity of the user. See FIG. 1. In another version, an internal fan (not shown) drives the molecules into a tube (7) that connects the opening of the sapphire vial to the user's nostrils. See FIG. 2.

Figure 3:
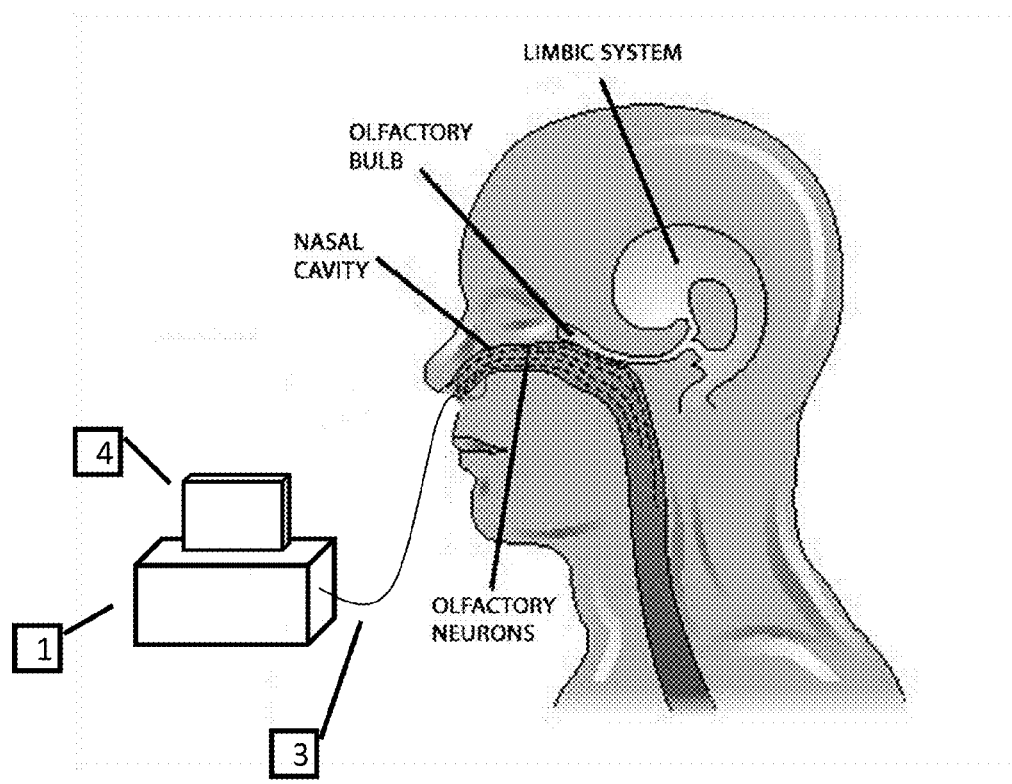
FIG. 3 shows aspects of a particular embodiment of the invention, as more particularly described in the specification.
Figure 3:
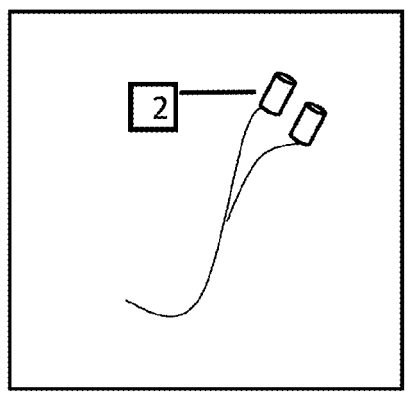

In another embodiment of the invention (see FIG. 3), a scent generator comprises an electronic device (1) powered by alternating current. The device includes one or two nostril inserts (2) composed of multiple sets of thermoresistive conducting film of amorphous carbon. The nostril inserts are connected to the base unit of the device by wires or some other electrical transmission medium (3). Electric current is passed through this film, thereby heating it and generating IR radiation. Each set of film may be tuned to a specific IR frequency based on the electrical modulation applied to it. The IR output is directed to the olfactory receptors of the user. Ideally, thermoresistive conducting film has little or no odor prior to its activation by the IR output. The base unit of the device also includes a simple computer (4) on which a proprietary olfaction software program has been installed. The program includes a drop-down list of scents that can be generated by the device. The frequencies of the IR output are tuned based on the scent selected from the drop-down list. The user selects a rose floral scent. The base unit of the device transmits to the thermoresistive conducting film on the nostril inserts the frequencies and amplitudes of a rose floral scent. The user perceives the scent of roses until the electrical current to the film is interrupted. In an alternate version of this embodiment, multiple nostril-insert units can be connected to the body of the device through optional TS or TRS connectors so that multiple users can share the same scent experience. Alternatively, each nostril insert may receive a different set of frequencies and amplitudes from the base unit, thereby producing different scent experiences for each user. In addition, the connection between the base unit and the nostril inserts could be wireless. The nostril inserts could also have multiple end-to-end holes or one large central hole to facilitate breathing.

Figure 4:
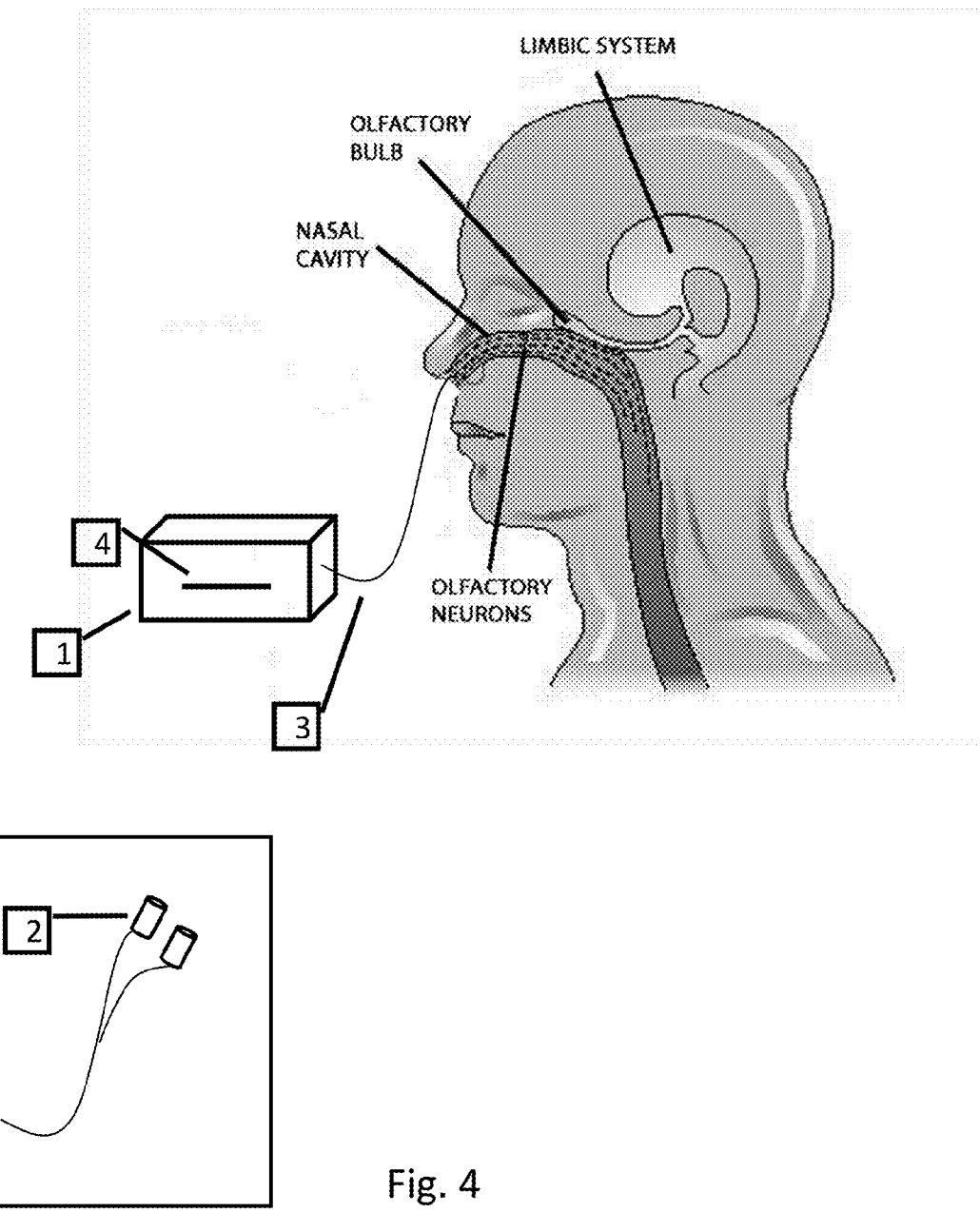
FIG. 4 shows aspects of a particular embodiment of the invention, as more particularly described in the specification.

In yet another embodiment of the invention (see FIG. 4), a scent generator comprises an electronic device (1) powered by alternating current. The device comprises a tunable diode laser. Multiple diodes are used, permitting the simultaneous generation of multiple laser frequencies. The laser output is directed to the olfactory receptors of the user by means of two nostril inserts (2). The nostril inserts are connected to the laser output of the base unit by optical fiber or any other form of optical waveguide (3). The base unit of the device also includes a read-only optical drive, such as a CD or DVD drive. The user selects an optical disc and inserts it into a slot (4) in the base unit of the device. The optical disc contains a composition of scent frequencies and amplitudes with a running time of 60 minutes. The composition is entitled "A Day in Provence." The base unit of the device generates laser outputs based on the scent frequencies and amplitudes embodied on the optical disc. The outputs are delivered to the user's olfactory receptors via the optical fiber or other waveguide inserted into the nostrils. The user dons a satin eye mask and ear plugs, lies back in an overstuffed recliner, and is carried by the composition through a concatenation of fragrances indigenous to the regions of southern France. C'est magnifique!

One of ordinary skill in the art would recognize many other variations, modifications, and alternatives. The above examples are merely illustrations, which should not unduly limit the scope of the claims herein. It is also understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A method for generating a scent comprising:
providing at least one electromagnetic radiation device,
wherein the device is configured to generate a first set of at least one predetermined frequency of electromagnetic radiation,
when the first set is applied to an element, a first scent is generated, and
the first scent is not an inherent characteristic of the element.

2. The method of claim 1 wherein at least one predetermined frequency is within the infrared spectrum.

3. The method of claim 1 wherein the element comprises atmosphere.

4. The method of claim 1 wherein the element comprises a liquid at room temperature.

5. The method of claim 1 wherein the element comprises an oil.

6. The method of claim 1 wherein the first set comprises one of two, three, four, or five different frequencies.

7. A method for generating a scent comprising:
providing at least one electromagnetic radiation device,
wherein the device is configured to generate a first set of at least one predetermined frequency of electromagnetic radiation at a first point in time and a second set of at least one predetermined frequency of electromagnetic radiation at a second point in time,
when the first set is applied to an element, a first scent is generated,
when the second set is applied to the element, a second scent is generated,
at least one frequency of the second set is not included in the first set,
at least one characteristic of the second scent is not included in the first scent, and
the element to which the first set is applied is the same element to which the second set is applied.

8. The method of claim 7 wherein at least one predetermined frequency is within the infrared spectrum.

9. The method of claim 7 wherein the element comprises atmosphere.

10. The method of claim 7 wherein the element comprises a liquid at room temperature.

11. The method of claim 7 wherein the element comprises an oil.

12. The method of claim 7 wherein at least one of the first set and the second set comprises one of two, three, four, or five different frequencies.

13. A method for generating a scent comprising:
providing at least one electromagnetic radiation device,
wherein the device is configured to generate a first set of at least one predetermined frequency of electromagnetic radiation, and
when the first set is applied to at least one olfactory receptor of the user, the user experiences a first scent.

14. The method of claim 13 wherein at least one predetermined frequency is within the infrared spectrum.

15. The method of claim 13 wherein at least one of the first set and the second set comprises one of two, three, four, or five different frequencies.

16. A method for generating a scent comprising:
providing at least one electromagnetic radiation device,
wherein the device is configured to generate a first set of at least one predetermined frequency of electromagnetic radiation at a first point in time and a second set of at least one predetermined frequency of electromagnetic radiation at a second point in time,
when the first set is applied to at least one olfactory receptor of the user, the user experiences a first scent,
when the second set is applied to at least one olfactory receptor of the user, the user experiences a second scent,
at least one frequency of the second set is not included in the first set, and
at least one characteristic of the second scent is not included in the first scent.

17. The method of claim 16 wherein at least one predetermined frequency is within the infrared spectrum.

18. The method of claim 16 wherein at least one of the first set and the second set comprises one of two, three, four, or five different frequencies.

* * * * *